(12) United States Patent
Isenberg et al.

(10) Patent No.: US 12,359,155 B2
(45) Date of Patent: Jul. 15, 2025

(54) HIGHLY DEFORMABLE POROUS MEMBRANE CULTURE SYSTEM AND ACTUATION METHODS FOR STUDYING THE EFFECTS OF BIOMECHANICAL STRETCH ON CULTURED TISSUE

(71) Applicant: The Charles Stark Draper Laboratory Inc., Cambridge, MA (US)

(72) Inventors: Brett Isenberg, Newton, MA (US); Joseph Charest, Jamaica Plain, MA (US); Corin Williams, Framingham, MA (US); Ernest Kim Soonho, Cambridge, MA (US); Morgan Pilkenton, Sommerville, MA (US); Patrick Davis, Sommerville, MA (US); Elizabeth Ellen Marr, Brookline, MA (US); Else Marie Vedula, Stoneham, MA (US)

(73) Assignee: The Charles Stark Draper Laboratory Inc.

( * ) Notice: Subject to any disclaimer, the term of this patent is extended or adjusted under 35 U.S.C. 154(b) by 552 days.

(21) Appl. No.: 17/238,501

(22) Filed: Apr. 23, 2021

(65) Prior Publication Data

US 2022/0340848 A1    Oct. 27, 2022

(51) Int. Cl.
*C12M 1/32*     (2006.01)
*B01L 3/00*     (2006.01)
(Continued)

(52) U.S. Cl.
CPC ......... *C12M 23/12* (2013.01); *B01L 3/50851* (2013.01); *B01L 3/50853* (2013.01); *C12M 23/22* (2013.01); *C12M 25/04* (2013.01)

(58) Field of Classification Search
CPC ...... C12M 23/12; C12M 23/22; C12M 25/04; B01L 3/50851; B01L 3/50853
(Continued)

(56) References Cited

U.S. PATENT DOCUMENTS 7,646,544 B2 * 1/2010 Batchko ................. B33Y 50/02
                                                    359/666
2004/0069717 A1  4/2004 Laurell et al.
(Continued)

FOREIGN PATENT DOCUMENTS

EP          2 639 293 A1    9/2013
WO    WO-2020/013851 A1    1/2020
(Continued)

OTHER PUBLICATIONS

International Search Report and Written Opinion on PCT Appl. Ser. No. PCT/US2022/025949 dated Sep. 15, 2022 (17 pages).
(Continued)

*Primary Examiner* — Michael L Hobbs
*Assistant Examiner* — Lenora A Abel
(74) *Attorney, Agent, or Firm* — Foley & Lardner LLP

(57) ABSTRACT

The systems and methods of the present disclosure provide highly deformable porous membrane culture systems and actuation methods for studying the effects of biomedical stretch on cultured tissue. A well plate can include a well having a first opening configured to receive an insert coupled to a deformable membrane. The well plate can include a gasket positioned within the well and configured to create a seal between the insert and the well when the insert is positioned in the well. The well plate can include a chamber defined beneath the well, the chamber configured to receive fluid media and to expose the fluid media to a surface of the deformable membrane when the insert is positioned in the well. The well plate can include an actuator
(Continued)

configured to stretch the deformable membrane by a target amount of strain.

11 Claims, 13 Drawing Sheets

(51) Int. Cl.
    *C12M 1/00*      (2006.01)
    *C12M 1/12*      (2006.01)

(58) Field of Classification Search
    USPC ................................................. 435/297.5
    See application file for complete search history.

(56) References Cited

U.S. PATENT DOCUMENTS

| | | | | |
|---|---|---|---|---|
| 2007/0166817 | A1* | 7/2007 | Wilkes | C12M 35/04 |
| | | | | 435/297.5 |
| 2010/0273258 | A1 | 10/2010 | Lannutti et al. | |
| 2013/0059324 | A1* | 3/2013 | Sittampalam | C12M 35/04 |
| | | | | 435/29 |
| 2013/0337565 | A1 | 12/2013 | Banes et al. | |
| 2015/0050722 | A1* | 2/2015 | Simmons | C12M 23/12 |
| | | | | 435/305.2 |
| 2020/0087608 | A1 | 3/2020 | Ingber et al. | |
| 2020/0270561 | A1 | 8/2020 | Marino et al. | |
| 2020/0354668 | A1 | 11/2020 | Sawyer et al. | |

FOREIGN PATENT DOCUMENTS

| | | |
|---|---|---|
| WO | WO-2020/023904 A1 | 1/2020 |
| WO | WO-2020/109865 A1 | 6/2020 |

OTHER PUBLICATIONS

International Preliminary Report on Patentability on PCT Appl. Ser. No. PCT/US2022/025949 dated Nov. 2, 2023 (11 pages).

* cited by examiner

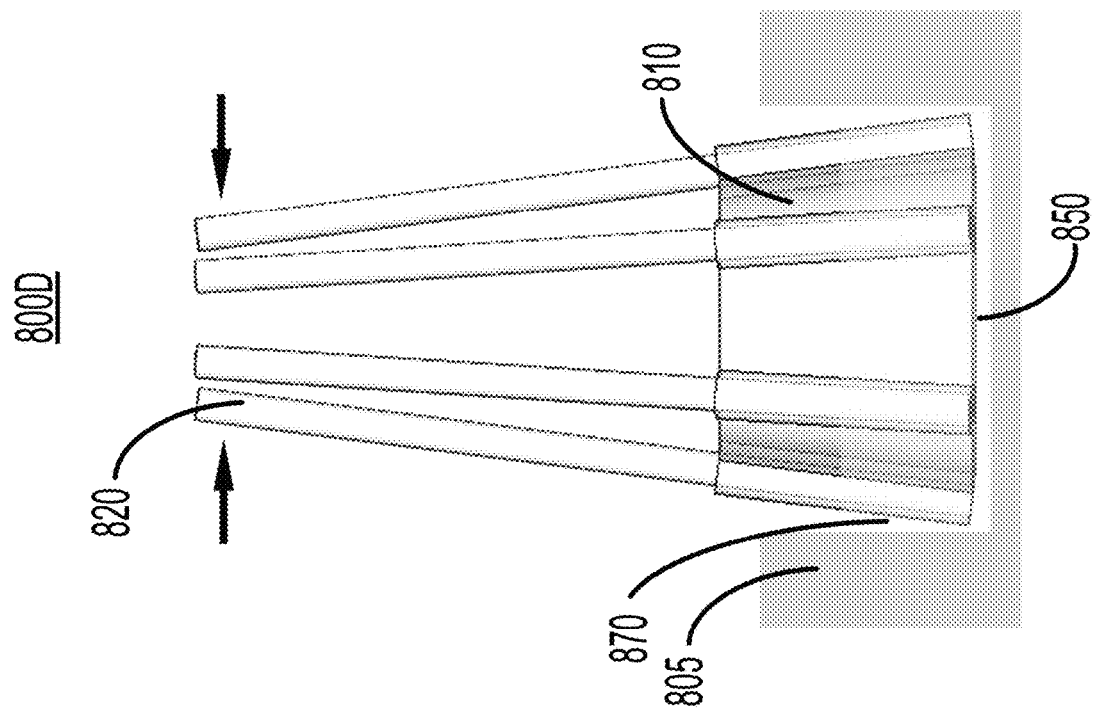
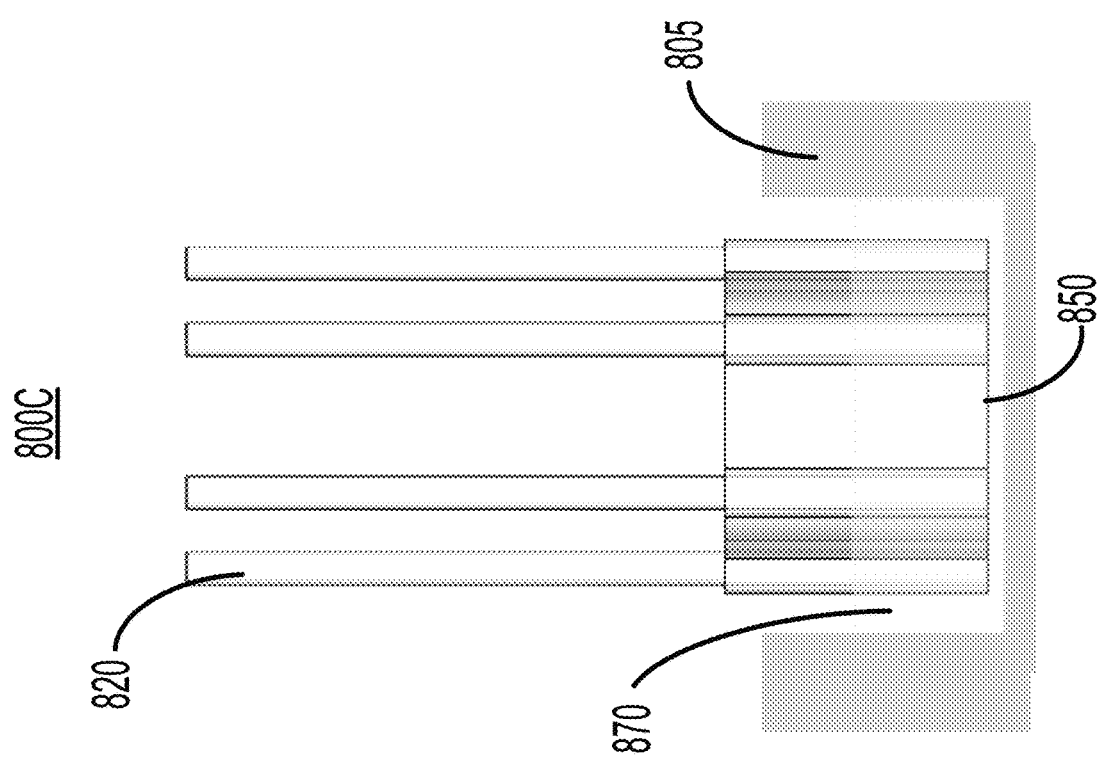

HIGHLY DEFORMABLE POROUS MEMBRANE CULTURE SYSTEM AND ACTUATION METHODS FOR STUDYING THE EFFECTS OF BIOMECHANICAL STRETCH ON CULTURED TISSUE

BACKGROUND

Cell cultures, such as cell cultures for tissues, can be grown to study infectious diseases. It can be challenging to grow cell cultures that mimic the environments experienced by human tissue.

SUMMARY

Urinary tract infections (UTIs) are among the most common infectious diseases worldwide, but still significantly understudied. Bacteria, such as uropathogenic *E. coli* (UPEC), account for a major proportion of UTI. Given the substantial economic burden of UTI treatment, and increasing antibiotic resistance, there is an urgent need to better understand UTI pathology. Most models developed for UTI use murine infection; few human-relevant models exist. Other implementations of UTI models have utilized cells in static culture, however, it is important to study UTI etiology in the context of the unique aspects of the bladder's biophysical environment (e.g., urine, flow, stretch). For example, fluid flow can significantly affect bacterial binding and it is hypothesized that mechanical stretch increases the endo/exocytosis behavior of bladder epithelial cells that may be hijacked by bacteria in UTI. The effect of mechanical stimulation of the bladder tissue on the progression of UTIs, including wall stretch during filling and flow-induced shear stress during voiding, has been poorly studied largely due the lack of in vitro high-throughput, complex culture platforms that can accurately and repeated apply such stimulation to cultured bladder tissues. In addition, stretch is an element of many human and mammalian tissues, therefore an apparatus to provide stretch to culture tissue provides a means to better mimic the conditions of in vivo generally.

The systems and methods of this technical solution provide highly deformable porous membrane culture systems and actuation methods for studying the effects of biomechanical stress on cultured tissue. A custom culture well is provided that includes a highly deformable, porous membrane that divides the well into two compartments. Cells are seeded onto this membrane and allowed to grow into mature tissue. Cell culture media, or other biological fluids, are placed both above and below this membrane to ensure proper growth and maintenance of the cells. The pores in the membrane allow for transport of constituents between the two compartments separated by the membrane. The cells can be mechanically stimulated by actuating the deformable membrane to which they are attached by any of the techniques described herein. In addition to membrane deformation, the cells on the membrane are also subjected to controlled fluid shear stress by moving fluid across the face of the membrane via an integrated pumping mechanism or an externally connected pumping system.

At least one aspect of the present disclosure is directed to a well plate for actuating cell culture membranes. The well plate can include a well comprising a first opening. The first opening can receive an insert coupled to a deformable membrane. The well plate can include a gasket positioned within the well and configured to create a seal between the insert and the well when the insert is positioned in the well. The well plate can include a chamber defined beneath the well. The chamber can receive fluid media and to expose the fluid media to a surface of the deformable membrane when the insert is positioned in the well. The well plate can include an actuator configured to stretch the deformable membrane by a target amount of strain.

In some implementations, the gasket can include an O-ring and a collar. In some implementations, the collar can couple the insert to the well and the O-ring configured to create a seal between the collar and the well. In some implementations, a surface of the chamber is defined by a transparent window that provides an optical interface to the chamber and to the surface of the deformable membrane when the insert is positioned in the well. In some implementations, the well further comprises a connector configured to receive and couple to the insert. In some implementations, the actuator comprises a mechanical iris configured to couple to the insert when the insert is positioned within the well, and to radially stretch the deformable membrane by the target amount of strain.

In some implementations, the actuator comprises a rim that is similar in size to a boundary of the deformable membrane of the insert, and is configured to cause the deformable membrane to stretch over the rim by the target amount of strain when the insert is positioned in the well. In some implementations, the actuator comprises a pin configured to press into the deformable membrane of the insert when the insert is positioned in the well, such that the pin deforms the deformable membrane by the target amount of strain when the insert is positioned in the well. In some implementations, the actuator comprises a magnet positioned within a predetermined distance from the insert when the insert is positioned within the well, such that a magnetic force between the magnet and one or more magnetic particles in the deformable membrane causes the deformable membrane to stretch by the target amount of strain when the insert is positioned in the well.

In some implementations, the chamber further comprises an inlet port configured to couple to a pressure controller that provides the fluid media at a target pressure. In some implementations, the inlet port can receive the fluid media such that the fluid media causes the deformable membrane of the insert to stretch by the target amount of strain when the insert is positioned in the well. In some implementations, the well plate can include a second well comprising a second opening. In some implementations, the second opening can receive a second insert coupled to a second deformable membrane. In some implementations, a second actuator configured to stretch the second deformable membrane by a second target amount of strain.

At least one other aspect of the present disclosure is directed to a system for culturing cells on stretchable membranes. The system can include a well plate comprising a well having a first opening at a surface of the well plate and a second opening to a chamber beneath the well. The system can include a transparent layer coupled to the well plate opposite the surface of the well plate. The transparent layer can define a first surface of the chamber beneath the well and provide an optical interface to the well. The system can include a deformable membrane within the well. The deformable membrane can include a first membrane surface exposed via the first opening and a second membrane surface exposed to the chamber beneath the well. The system can include an actuator configured to stretch the deformable membrane by a target amount of strain.

In some implementations, the system can include a second well defined in the well plate. In some implementations, the second well having a third opening at the surface of the well plate. In some implementations, the system can include a second deformable membrane within the well having a third membrane surface exposed via the third opening. In some implementations, the system can include a second actuator configured stretch the second deformable membrane by a second target amount of strain, independent of the actuator stretching the deformable membrane by the target amount of strain. In some implementations, the actuator comprises a mechanical iris coupled to the deformable membrane. In some implementations, the mechanical iris configured to radially stretch the deformable membrane by the target amount of strain.

In some implementations, the actuator comprises a rim that is similar in size to a boundary of the deformable membrane. In some implementations, the rim is configured to move such that the deformable membrane stretches over the rim by the target amount of strain. In some implementations, the actuator comprises a pin configured to press into the deformable membrane such that the pin deforms the deformable membrane by the target amount of strain. In some implementations, the deformable membrane comprises one or more magnetic particles. In some implementations, the actuator comprises a magnet positioned within a predetermined distance from the deformable membrane such that a magnetic force between the magnet and the one or more magnetic particles causes the deformable membrane to stretch by the target amount of strain.

At least one other aspect of the present disclosure is directed to an insert for a well plate. The insert can include a housing configured to be inserted into and create a seal with a well of a well plate. The insert can include a deformable membrane coupled to the housing configured to culture cells. The insert can include a cell culture chamber defined by the housing and a surface of the deformable membrane. The cell culture chamber exposed via a first opening in the housing.

In some implementations, the deformable membrane comprises one or more pores that are each sized to support culturing of tissue samples while the deformable membrane is stretched by a target amount of strain. In some implementations, the housing comprises one or more flexible walls coupled to the deformable membrane. In some implementations, the one or more flexible walls are configured to be moved by an actuator of the well plate, causing the deformable membrane to stretch by the target amount of strain. In some implementations, the deformable membrane is configured to stretch along at least one dimension by greater than fifteen percent of a non-deformed size of the deformable membrane.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. The foregoing and other objects, aspects, features, and advantages of the disclosure will become more apparent and better understood by referring to the following description taken in conjunction with the accompanying drawings, in which:

FIGS. 8C and 8D illustrate cross-sectional views of the example actuation technique shown in FIGS. 8A and 8B, in accordance with one or more implementations.

DETAILED DESCRIPTION

Figure 1:
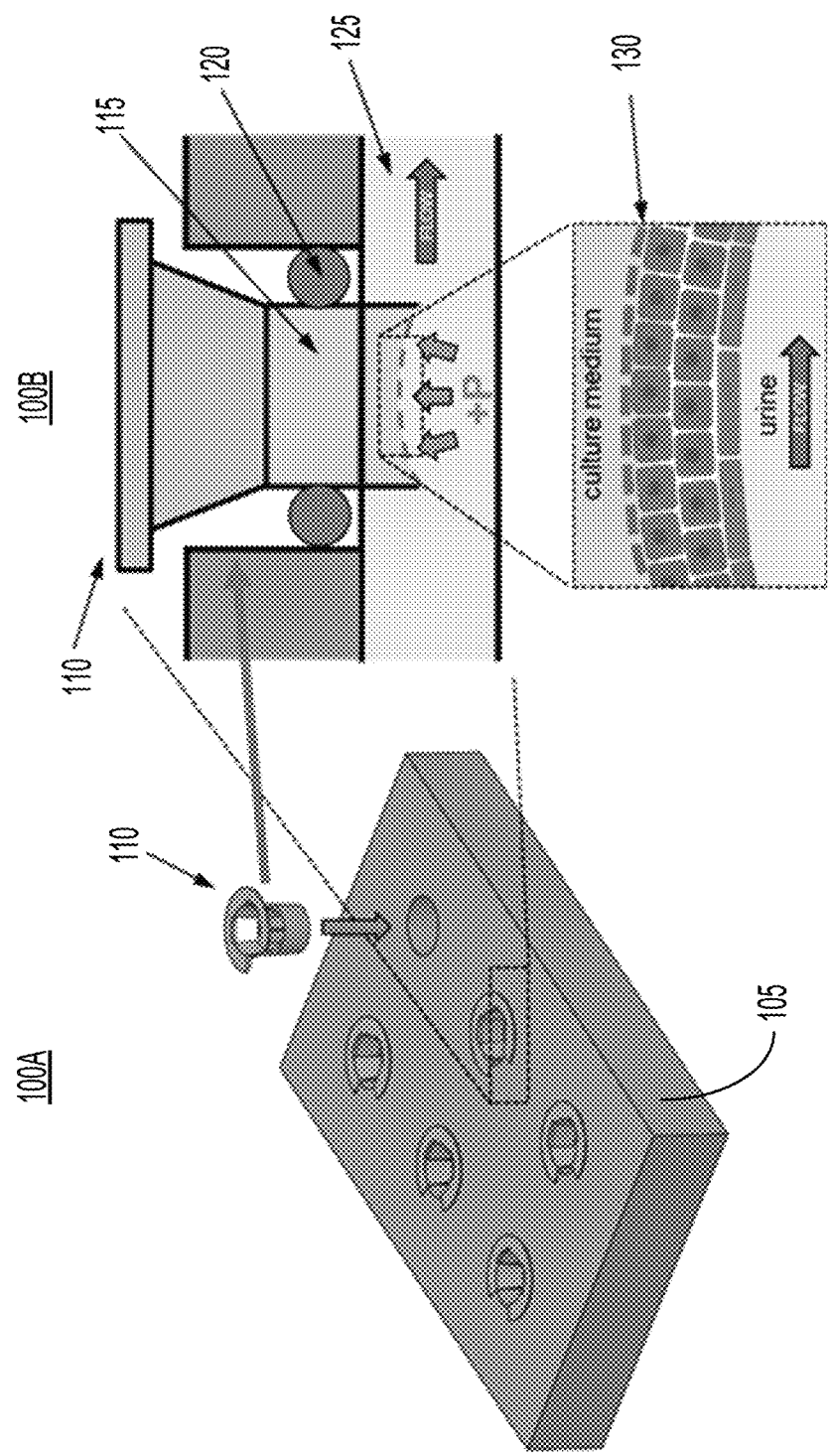
FIG. 1 illustrates example perspective and cross-sectional views of a highly deformable porous membrane culture system, in accordance with one or more implementations.

The various concepts introduced above and discussed in greater detail below may be implemented in any of numerous ways, as the described concepts are not limited to any particular manner of implementation. Examples of specific implementations and applications are provided primarily for illustrative purposes.

As described herein above, the UTIs are common infections that are significantly understudied. Other cell culturing systems often use murine models or models that do not accurately mimic the conditions of in vivo. For UTIs in particular, mimicking the environment that cells in bladder tissue experience is important, because it is hypothesized that mechanical stretch increases the endo/exocytosis behavior of bladder epithelial cells that may be hijacked by bacteria in UTIs. In addition, stretch is an element of many human and mammalian tissues, therefore an apparatus to provide stretch to culture tissue provides a means to better mimic the conditions of in vivo.

The system and methods of this technical solution provide a custom culture well that includes highly deformable, porous membrane that divides the well into two compartments. Cells can be seeded onto this membrane (e.g., using various cell seeding techniques, etc.) and allowed to grow into mature tissue. Cell culture media or other biological fluids can be placed both above and below this membrane to ensure proper growth and maintenance of the cells. The pores allow for transport of constituents between the two compartments separated by the membrane. The cells can be mechanically stimulated by actuating the deformable membrane to which they are attached by any of the methods described herein. In addition to membrane deformation, the cells on the membrane are also subjected to controlled fluid shear stress by moving fluid across the face of the membrane (e.g., via an integrated pumping mechanism or an externally connected pumping system, etc.).

The membranes described herein can be deformable and porous. The membranes can be constructed from materials including, but not limited to, polydimethylsiloxane, polyurethane, natural rubber, and so-called "tough" hydrogels. The membrane can be actuated in the well plate using the various techniques described herein. One such technique is pneumatic actuation. In pneumatic actuation techniques, the cell culture substrates can be confined to a well via an airtight seal between the substrate and the wall of the well. Media or fluid exchange in a lower well compartment can be achieved with fluidic ports connected to one or more pumps or devices that can provide fluid at a configurable pressure. This media line is also connected to a pressure source. As the media path is pressurized with positive or negative pressure the cell culture membrane deforms in a predictable manner.

Another such actuation technique is mechanical actuation. As an alternative to pressurizing to achieve deformation, the membrane can be stretched via contact with physical parts or mechanisms as described herein. One such approach is a drum head and hoop approach. This approach is based on the tensioning and tuning of a musical drum. In this approach, the flexible membrane can be affixed to a hoop, then stretched over a rim. The hoop and rim can move relative to each other such that the membrane is pulled further down the rim, resulting in mostly isotropic strain of the membrane. Linear actuation of the hoop-rim motion can be accomplished by a variety of actuators—an electromechanical actuator, a magnet, or a hydraulic or pneumatic mechanism, among others. Another mechanical approach is an approach based on a pin array. In this approach, a pin can be pressed onto the center of each cell culture membrane to a precise depth to stretch the cell culture membrane by a desired amount of strain. Miniature actuators can allow individual control such that each membrane can be stretched to a different desired amount of strain.

The desired amount of strain can be a target amount of strain, or an amount by which the membrane should stretch in response to actuation. Mechanical strain is a geometric measure of deformation representing the relative displacement between particles in a material body, such as the particles that make up the membranes described herein. When the membrane is subjected to external forces (e.g., via the actuation methods described herein), the membrane can deform and increase in size along one or more dimensions. The strain of the membrane can be calculated as a ratio of the change in size of the membrane to the original size of the membrane prior to actuation. Thus, as described herein, the "desired amount of strain" or "target amount of strain" can include or refer to a desired or target amount of stretch (e.g., a total amount of increase in size, etc.), or a desired or target amount of deformation of the membrane. The desired or target amount of strain can be predetermined amount of strain by which the membrane should be stretched. In some implementations, the target amount of strain can be determined based on the properties of the cells or tissue samples being cultured on the membrane.

Another approach to mechanical actuation includes using a mechanical iris to uniformly stretch the membrane by a number of points about the perimeter of the membrane. For example, a mechanical iris (similar to those used in camera shutters, or other such apertures) can couple to eight points around the perimeter of the cell culture membrane. The mechanical iris can actuate (e.g., manually or via a motor, etc.) and pull uniformly on the perimeter of the cell culture membrane. The iris can be partially opened or closed to cause the cell culture membrane to stretch by the desired amount of strain. As described herein above, the well plate can include many wells, and each well can have its own actuation mechanism. Thus, each well can be actuated independently, with each well having its own desired amount of strain. This can be useful for comparing the effects of strain on similar cultures under similar conditions (e.g., in the same well plate, etc.). In some implementations, any of the wells can include any of the actuation devices described herein. For example, one well can include a mechanical iris actuation type, and another well can include a pin that presses into the cell culture membrane for that well.

Another actuation technique to stretch the cell culture membrane is a magnetic actuation technique. Magnetic actuation can allow for a non-contact method of deforming the membrane with reduced mechanical complexity. In such an approach, a cell culture membrane can be embedded with magnetic or ferromagnetic particles or beads encapsulated in an inert material. The particles can be dispersed through the membrane in a controlled configuration. An array of magnetic or electromagnetic pins, or a single large magnet or electromagnet, can be brought into the appropriate proximity to the membrane, resulting in attraction or repulsion. This deformation results in membrane strain. The magnet can be positioned at a predetermined distance that applies an appropriate amount of magnetic force on the membrane to achieve the desired amount of strain. Membrane strain displacement can be controlled precisely if the particles are placed precisely. In addition, instead of embedded particles, a ferrous mechanical feature can be included on top of, affixed to the bottom, or embedded within the membrane. This mechanical feature could be a ring, toroid or other circular shape. The mechanical feature can also be a set of features, such as a circle of small objects affixed to the membrane around about the perimeter of the membrane.

To better control the amount of membrane strain, a detent or mechanical holding apparatus can limit the amount of stretch. The detent can be a ledge, barrier, or surface feature that limits the amount of distance the membrane can stretch. The detent can also be configured in steps, ramps, or other ways to progressively or incrementally increase or decrease the resistance of the membrane to motion, strain, or stretch. In a magnetic actuation approach, the magnet can be an electromagnet, and the amount of current applied to the electromagnet can adjust the magnetic field to change the strain of the cell culture membrane. The strength of the electromagnet can be adjusted by changing the current, voltage, duty cycle, frequency, or other parameter of the electrical signal that creates the electromagnet.

Any of the actuation methods described herein can be integrated with the well plates or wells described herein. The well plates or wells described herein can also each be integrated with controlled fluid flow to either side of the membrane to induce shear stimulation of the cells or tissues cultured on the membrane. Relevant tissue models that can be used with the systems and methods described herein can include any tissue that responds to or experiences stretch in vivo, such as bladder tissue. Further, any tissues where stretch could be used to investigate aspects of the tissue or diseases associated with the tissue can be cultured and studied using the techniques described herein. Some examples include, but are not limited to, cardiac tissue, vascular tissue, muscle tissue, diaphragm tissue, lung tissue, uterus tissue, gut tissue, esophagus tissue, connective tissue, or skin tissue, among others.

FIG. 1 illustrates example perspective and cross-sectional views 100A and 100B, respectively, of a highly deformable porous membrane culture system, in accordance with one or more implementations. The perspective view 100A shows a well plate 105. The well plate 105 can include one or more wells that can each receive an insert 110. The wells of the well plate 105 can be arranged in any particular manner across a surface of the well plate 105, such as a rectangular grid pattern or a straight line pattern. Thus, although the well plate 105 is shown as including six individual wells that can each receive an insert 110, it should be understood that the well plate 105 can be designed into include any number of wells in any arrangement. Each well in the well plate 105 can include one or more fasteners or connectors that serve to receive and couple to an insert 110. In some implementations, the features of the insert 110 can be included in the wells of the well plate directly, that is, the well itself can include the functional features of the insert 110 as described herein.

The insert 110 can include a deformable membrane on which cells or tissue samples can be cultured. The deformable membrane can be formed as a part of, or coupled to, the insert 110. The insert 110 can include a housing that includes one or more connectors, such as a snap-fit connector, a friction fit connector, a press-fit connector, a threaded connector, or any other type of connector, which can couple to a well of the well plate 105. The connector of the housing for the insert 110 can also disconnect from the well of the well plate 105, such that the insert can be replaced with another insert 110. In some implementations, the insert 110 is permanently affixed to the well of the well plate 105 following insertion. Further details of the well plate 105, the wells defined therein, and the insert 110 are shown in view 100B.

The view 100B shows a perspective view of the insert 110 following insertion to the well of the well plate 105. The view 100B shows culture media 115, a gasket 120, fluid flow 125, and (in the zoomed-in cross-section) a deformable membrane 130. The culture media 115 can be any form of culture media that can support the culturing of cells or tissue samples present on the deformable membrane 130. As shown, the cells have been seeded on the bottom portion of the deformable membrane 130. However, it should be understood that cells or tissue samples can be seeded or cultured on any surface of the deformable membrane 130. The culture media 115 can be disposed within the housing of the insert 110 above the deformable membrane 130. The deformable membrane 130 can be manufactured to be semi-permeable, with a permeability that permits the culture media 115 to pass through the deformable membrane 130 to support the cells growing on the deformable membrane 130. Thus, the culture media 115 can include water, nutrients, or other life-supporting fluids that can aid in the culturing of cells or tissue samples on the deformable membrane 130.

The view 100B shows that the deformable membrane 130 is deformed, or actuated, using the pneumatic (or hydraulic) actuation technique described herein above. In a pneumatic (or hydraulic) actuation-type system, the deformable membrane 130 is stretched by a desired amount of strain by the fluid flow 125. The fluid flow 125 can be provided by an external fluid source, which can pump the fluid flow 125 through a chamber formed in the well plate 105 beneath each well in the well plate 105 at a determined pressure. The pressure at which the fluid flow 125 is pumped through the well plate 105 can deform the deformable membrane 130 by the desired amount of strain, and the pressure can be modified (e.g., by changing the rate or pressure at which the pump or external fluid source provides the fluid, etc.) to deform the deformable membrane 130 by desired amounts. The fluid flow 125 can be any sort of fluid that can pass over the cells or tissue sample seeded or cultured on the deformable membrane 130. The fluid flow 125 can be, for example, a urine solution, or any other type of solution. The fluid flow 125 can subject the cells or tissue samples to controlled fluid shear stress by moving fluid across the face of the membrane at a desired speed. The fluid flow 125 can be provided by an integrated pumping mechanism (e.g., internal to or integrated with the well plate 105, etc.) or an externally connected pumping system.

When pneumatic or other pressure-based actuation techniques are used to deform the deformable membrane 130 by the desired amount of strain, a seal must be formed between the housing of the insert 110 and the well of the well plate 105. As shown in the view 100B, this seal is created by the gasket 120. The gasket 120 can be any sort of gasket or seal-creating fixture, such as an O-ring that surrounds the insert 110 when the insert 110 is inserted into the well of the well plate 105. In some implementations, the gasket 120 can be coupled to the outside of the housing of the insert 110 prior to the insert 110 being positioned within the well of the well plate 105. In such implementations, the gasket can rest or couple into a groove defined in the well of the well plate 105. Alternatively, the gasket 120 can be a feature of the well itself, and the housing of the insert 110 can have one or more grooves, slots, or other features that couple to the gasket 120 when the insert 110 is positioned in the well of the well plate 105.

The deformable membrane 130 can be manufactured to be semi-permeable, with a permeability that permits the culture media to pass through the deformable membrane 130 to support the cells growing on the deformable membrane 130. To provide the desired amount of permeability, the deformable membrane 130 can include one or more pores that allow selective passage of fluids, solutions, or other matter from one side of the deformable membrane to the other. Pore sizes, mesh spacing, or general transport properties of the deformable membrane 130 can be adjusted to control the relation between cell attachment, fluid flow, deformability, and pressure driving the fluid flow. In some implementations, the deformable membrane 130 can be designed for a desired hydraulic resistance along with cell attachment properties. In some implementations, the deformable membrane 130 can also be a porous mesh, gel, or other material that allows preferential transport of liquid through it while deforming to by desired amount of strain. The deformable membrane 130 can be formed via a subtractive manufacturing process, or via an electrospinning process, among others. A subtractive manufacturing process can include dissolving portions of a larger substrate, which can include filler material, to arrive at a final deformable membrane shape made of a material having desired mechanical properties. An electrospinning technique can include dissolving a polymer (e.g., such as polydimethylsiloxane (PDMS), etc.) in a solution. The solution can then be exposed to a high voltage potential at a nozzle of an electrospinning device, which can create solid fibers of the polymer material. The fibers can be woven together (e.g., or clumped, aggregated, or combined, etc.) to form the deformable membrane 130.

The deformable membrane 130 can also be coated, energetically treated via a plasma or other means, affixed with a self-assembled monolayer, surface deposited, or otherwise modified chemically to have chemical surface features to influence cell attachment, adhesion, spreading, or other cell properties. In some implementations, the deformable membrane 130 can have both mechanical and chemical surface features, with either or both such features placed on the scaffold in selected areas so that cell properties are modified within those areas. For example, some areas of the deformable membrane 130 can have a chemical surface modification to limit cell attachment while others would have a mechanical surface modification to encourage cell attachment.

Figure 2:
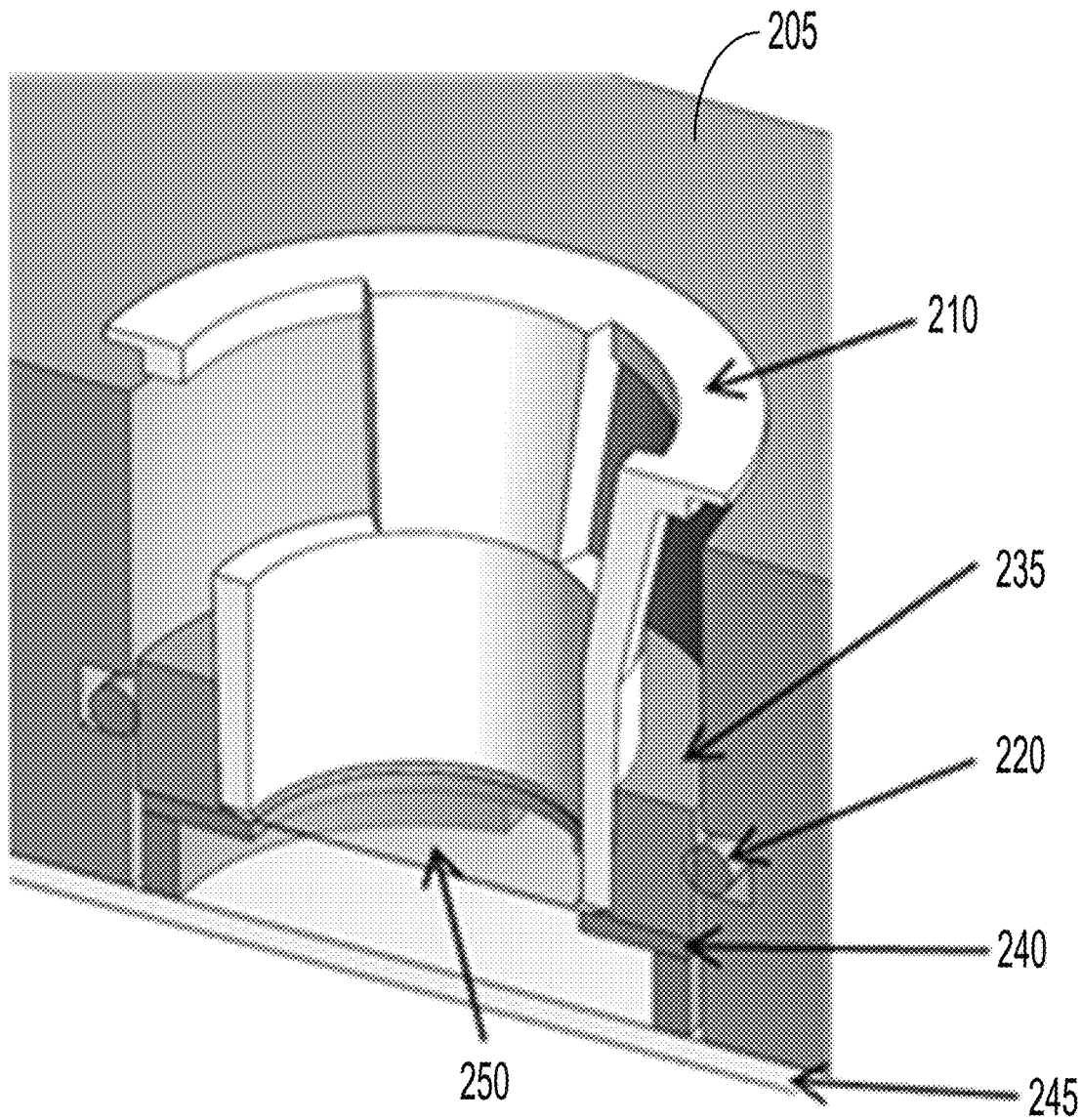
FIG. 2 illustrates cross-sectional view of an example well of a well plate having a highly deformable porous membrane, in accordance with one or more implementations.

FIG. 2 illustrates cross-sectional view 200 of an example well of a well plate 205 with an insert 210 positioned therein having a highly deformable porous membrane, in accordance with one or more implementations. The well plate 205 can be similar to, and include any of the functionality of, the well plate 105 described herein above in connection with FIG. 1. Likewise, the insert 210 can be similar to, and include any of the functionality of, the insert 110 described herein above in connection with FIG. 1. The cross-sectional view 200 shows a well of a well plate 205 with an insert 210 positioned therein. The insert 210 includes a deformable membrane 250. Within the well, a collar 235 surrounds the housing of the insert 210. The collar 235 can form a seal with the gasket 220, and thus form a seal between the insert 210 and the well of the well plate 205. A membrane clamp 240 affixes to and couples to the edges of the deformable membrane 250, aiding in the creation of a seal between the insert 210 and the well of the well plate 205. The chamber beneath the well can be defined both by a surface of the deformable membrane 250 and the transparent window 245.

As shown, the insert 210 includes and is coupled to the deformable membrane 250 at the bottom of the housing of the insert 210. Although both the insert 210 housing and the deformable membrane 250 are each shown as having a circular shape, it should be understood that other shapes are possible. The deformable membrane 250 can be coupled to the housing of the insert 210 such that the deformable membrane 250 forms a seal with the insert 210 housing. The deformable membrane 250 can be coupled to the insert 210, for example, using a type of adhesive material, or by thermoplastic bonding. As shown, the insert 210 housing can be open at the top, thereby exposing a surface of the deformable membrane 250 to an external environment. This can allow for observation and manipulation of the exposed surface of the membrane by external tools.

When the insert 210 is inserted into the well of the well plate 205, the collar 235, which can be positioned in and coupled to the well, surrounds the housing of the insert 210. The collar 235 can itself be a separate insert that couples to the well, and acts as a sealing buffer between the insert 210 and the well of the well plate 205. In some implementations, the collar 235 can be formed as part of the well of the well plate 205. The collar 235 can be made of a rubber, plastic, metallic, or composite material. In some implementations, the collar 235 can be a part of the insert 210. The collar 235 can form a seal with the gasket 220, and thus form a seal between the insert 210 and the well of the well plate 205. The gasket 220 can be similar to and include all of the functionality or structure of the gasket 220 described herein above in connection with FIG. 1. The gasket 220 can sit between the wall of the well of the well plate 205 and the collar 235. As shown, the gasket 220 can sit within a groove, or slot, formed in the wall of the well of the well plate 205. The gasket 220 can sit within the groove or slot along the perimeter of the well of the well plate 205. The gasket 220 can be manufactured from a rubber, plastic, or composite material, and can create an airtight or watertight seal between the collar 235 (or the insert 210, if the collar 235 is not used, etc.) and the well of the well plate 205. Thus, in using a gasket, any pressure provided in the chamber below the well of the well plate 205 can press on and deform the deformable membrane 250.

The membrane clamp 240 can be a barrier that defines the bottom of the well of the well plate, and can couples to the edges of the deformable membrane 250 when the insert 210 is positioned in the well of the well plate 205. The membrane clamp 240 can include one or more attachment features or connectors, which can couple to the bottom surface of the deformable membrane 250. The membrane clamp 240 can be positioned within the well of the well plate 205, and can conform to the shape of the outer perimeter of the deformable membrane 250. When the insert 210 is positioned into the well of the well plate 205, the insert 210 can fit tightly within the collar 235, and the deformable membrane 250 of the insert 210 can press against the membrane clamp 240. In some implementations, the membrane clamp 240 can press against the perimeter of the deformable membrane 250 to prevent the deformable membrane 250 from being removed (e.g., forced off of, etc.) the insert 210 when the deformable membrane 250 is stretched by the desired amount of strain.

The chamber beneath the well can be defined both by a surface of the deformable membrane 250 and the transparent window 245. As described herein above, the chamber beneath the well can allow a fluid flow, such as the fluid flow 125 described herein above in connection with FIG. 1, to be applied to the bottom surface of the deformable membrane 250. This can provide fluid shear stress to simulate an environment similar to in vivo. In addition, an optical interface into the chamber, and to the bottom surface of the deformable membrane 250, is provided by the transparent window 245. The transparent window 245 can be made out of any sort of sold, transparent material, such as glass, acrylic, or another type of clear polymer or plastic. As shown, the transparent window can define the bottom surface of the well plate 205. However, it should be understood that other arrangements are possible. For example, in some implementations, the transparent window 245 can form to only portion of a surface of the chamber beneath the well of the well plate 205. In some implementations, the transparent window 245 can be defined by a transparent sheet coupled to the bottom of the well plate 205.

Figure 3A:
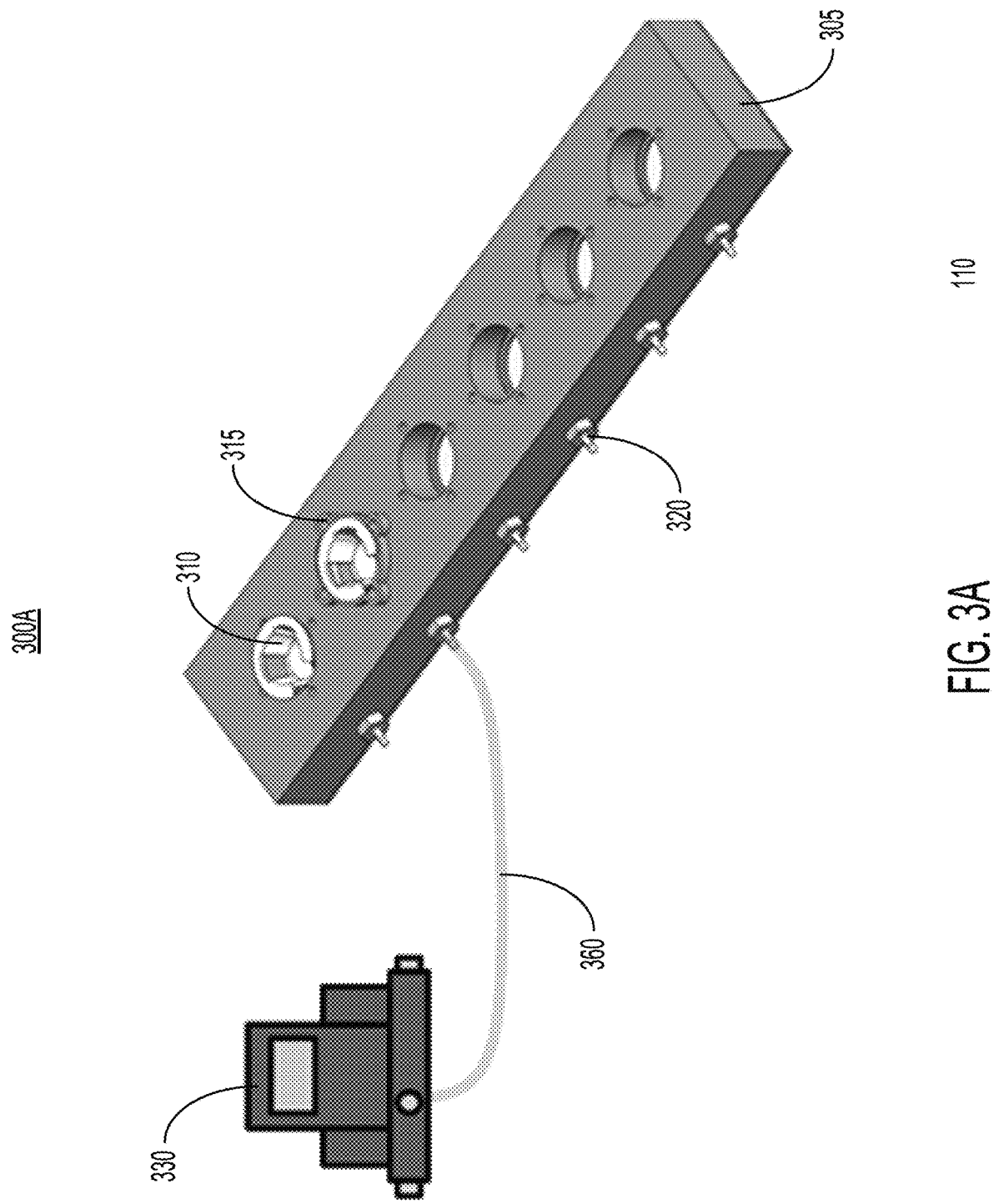
FIG. 3A illustrates a perspective view of a highly deformable porous membrane culture system that can be used with an external pump, in accordance with one or more implementations.

Referring now to FIG. 3A, illustrated is a perspective view 300A of a highly deformable porous membrane culture system that can be used with an external pump, in accordance with one or more implementations. As described herein above, an external pressure source, such as a pump, can be used in connection with the systems and methods described herein. The perspective view 300A shows a well plate 305 having six wells, with two inserts 310 positioned therein. One insert includes a coupling mechanism 315 that can couple the insert 310 to the well plate 305. The well plate 305 can include one or more inlet ports 320, which can be fluidly coupled to the chamber formed beneath a respective well by the insert 310 when the insert 310 is positioned in the well of the well plate 305. As further described herein, the fluid flow provided by the inlet ports into the chamber in each well can provide shear fluid force, which can mimic the conditions of in vivo. To provide the fluid flow, the inlet port can be coupled to a tube 360. The other end of the tube 360 can be coupled to a fluid source, such as the pump 330.

The well plate 305 can be similar to and include any of the structure or functionality of the well plates 105 or 205 described herein in connection with FIGS. 1 and 2, respectively. Likewise, the insert 310 can be similar to and include any of the structure or functionality of the inserts 110 or 210 described herein in connection with FIGS. 1 and 2, respectively. One insert includes a coupling mechanism 315 that can couple the insert 310 to the well plate 305. The well plate 305 can include one or more inlet ports 320, which can be fluidly coupled to the chamber formed beneath a respective well by the insert 310 when the insert 310 is positioned in the well of the well plate 305. As further described herein, the fluid flow provided by the inlet ports into the chamber in each well can provide shear fluid force, which can mimic the conditions of in vivo. To provide the fluid flow, the inlet port can be coupled to a tube 360. The other end of the tube 360 can be coupled to a fluid source, such as the pump 330.

Each of the inlet ports 320 can be fluidly coupled to a respective chamber defined beneath one of the wells of the well plate 305. Said another way, each well of the well plate can be provided with a fluid flow having its own pressure, flowrate, and fluid material. Thus, each well in the well plate 305 can have its own cell culturing environment, with different amounts of membrane strain and fluid shear flow experienced by each insert 310. In some implementations, one or more adjacent wells in the well plate 305 can share a chamber defined beneath the adjacent wells. Each of the wells having the shared chamber can receive a single fluid flow from a single tube 360. The tube 360 can be any sort of tube, pipe, or channel capable of transporting a fluid flow from a fluid source, such as the pump 330, to a well of the well plate 305. The pump 330 can be any sort of fluid pump that can provide a configurable fluid flow rate at configurable fluid pressure through the tube 360 and into the inlet of the well plate 305. In some implementations, a single pump 330 can provide fluid flows to each of the wells in the well plate 305. In some implementations, multiple pumps 330 can be used to deliver individual fluid flows to each of the wells in the well plate 330.

Figure 3B:
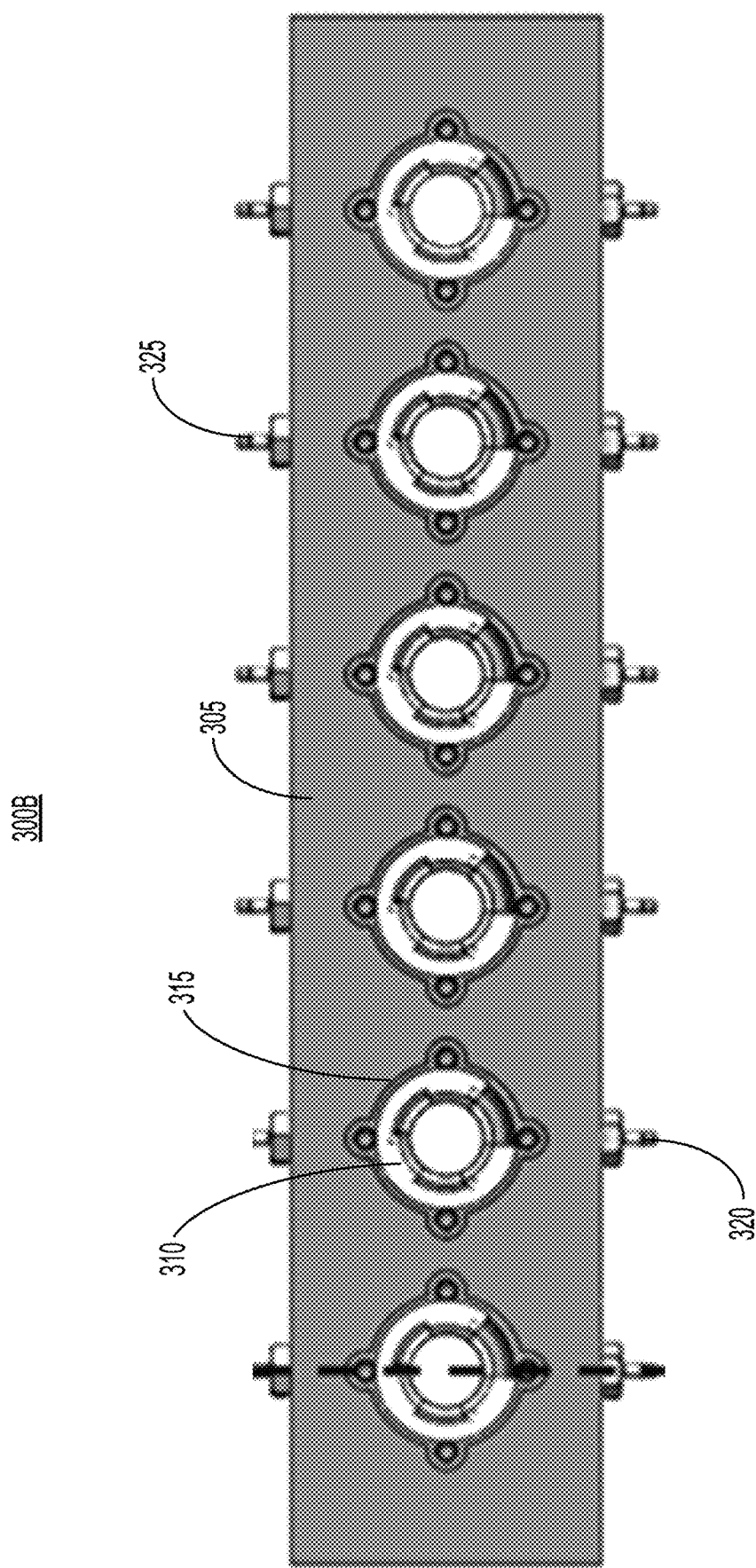
FIG. 3B illustrates a top view of the highly deformable porous membrane culture system depicted in FIG. 3A, in accordance with one or more implementations.

FIG. 3B illustrates a top view 300B of the highly deformable porous membrane culture system depicted in FIG. 3A. As shown in this view, each of the six wells in the well plate 305 is populated with an insert 310, each of which is coupled to a corresponding coupling mechanism 315. In addition, each of the wells in the well plate 305 is fluidly coupled to a respective inlet port 320 and a respective outlet port 325. As described herein above, the inlet port 320 of a well can receive a fluid flow from a fluid source at a respective pressure and a respective flow rate. Likewise, the fluid provided to the chamber beneath a well can exit the chamber via the outlet port 325. The outlet port 325 can be coupled to a fluid sink, such as a fluid reservoir. In some implementations, the chamber, the outlet port 325, and the inlet port 320 can be part of a closed-loop fluid system, where the fluid exiting the chamber via the outlet port can be processed, re-pressurized, and provided to the inlet port 320. A cross-sectional view of the chamber beneath a well in the well plate 305 is depicted in FIG. 3C.

Figure 3C:
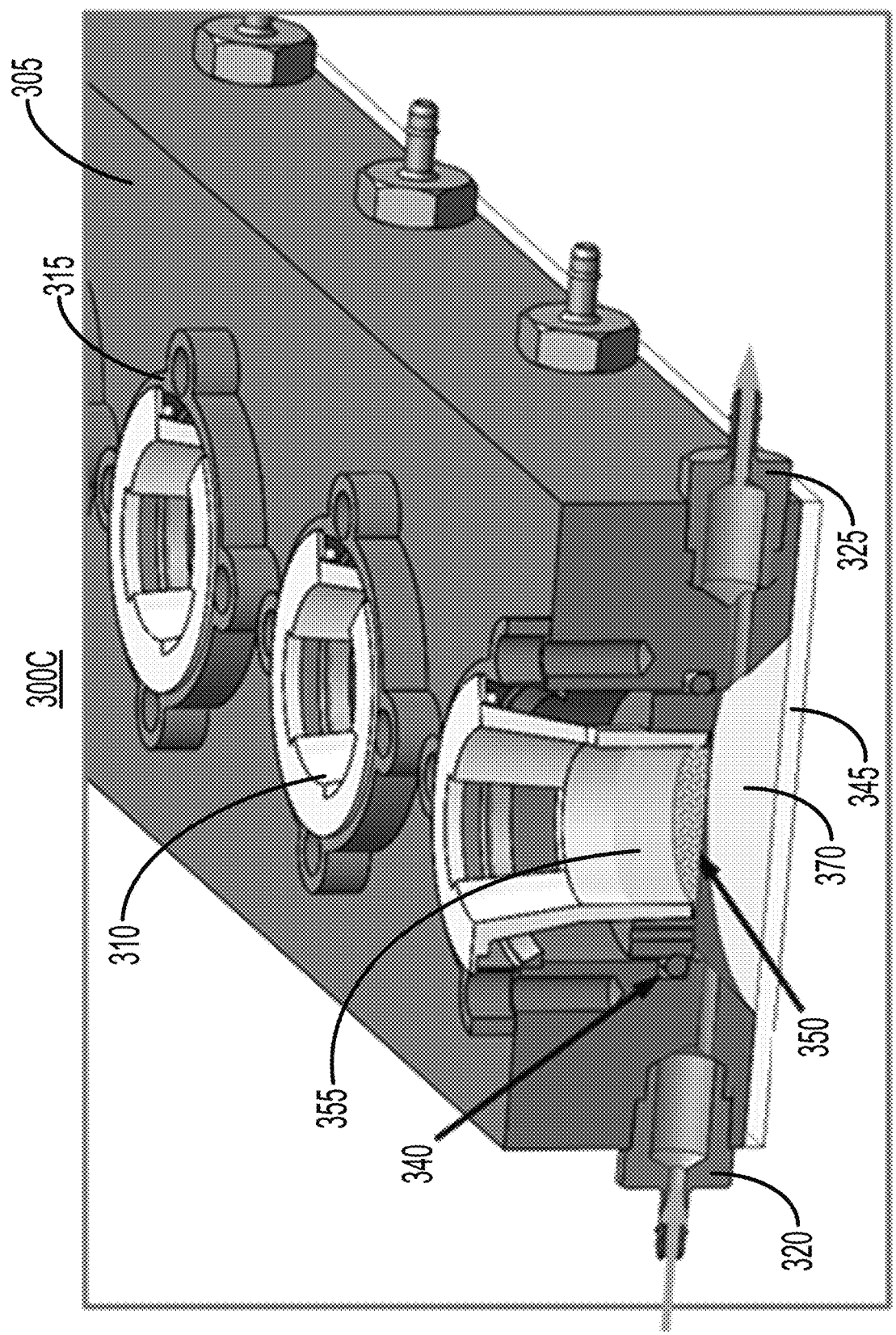
FIG. 3C illustrates a cross-sectional view of the highly deformable porous membrane culture system depicted in FIGS. 3A and 3B, in accordance with one or more implementations.

Referring now to FIG. 3C, illustrated is a cross-sectional view 300C of the highly deformable porous membrane culture system depicted in FIGS. 3A and 3B, in accordance with one or more implementations. The cross-sectional view depicts the chamber 370 beneath the well in the well plate 305. The view 300C shows the well plate 305, the inserts 310, the coupling mechanisms 315, the inlet ports 320, the outlet ports 325, the chamber 370, the deformable membrane 350, and the culture media 355.

As shown, the chamber 370 can be defined beneath the well of the well plate 305. The insert 310 can be positioned within the well above the chamber 370, such that the membrane 350 (which can be similar to and include all of the functionality of the deformable membrane 130 or 250 described herein in connection with FIGS. 1 and 2) forms a portion of a surface of the chamber, in contact with the fluid flow from the inlet port 320. Opposite the membrane is the transparent window 345, which can be similar to and include all of the structural and functional features of the transparent window 245. The transparent window 345 can provide an optical interface to the deformable membrane 350. The culture media 355 can be provided on the opposite side of the deformable membrane 350 from the chamber 370. The culture media can be similar to and include any of the features of the culture media 115 described herein above in connection with FIG. 1. The culture media 355, and the deformable membrane 350, can be exposed via the opening of the insert 310.

As indicated by the arrows, the fluid flow can pass from the inlet port 320, through the chamber 370 (where it makes contact and applies a shear force to the deformable membrane 350), and of the system via the outlet port 325. Each of the inlet ports 320 and the outlet ports 325 on the well plate 305 can include a connector, such as a threaded connector, a press-fit connector, a friction fit connector, or a Luer-lock connector, among others, that can couple to a pipe or tube, such as the tube 360 described herein above. The well plate 305 can be used in conjunction with any of the actuation methods described herein. The well plate 305 can provide pneumatic or hydraulic actuation (e.g., via the inlet ports 320 and the outlet ports 325, etc.), mechanical actuation using a mechanical iris (not pictured), a hoop-and-ring technique (described in greater detail below in connection with FIG. 4), or a pin array (described in greater detail below in connection with FIG. 5). The well plate 305 can further be used in connection with other actuation techniques, such as magnetic actuation. Thus, the well plate 305 can stretch the deformable membrane 350 using any of the techniques described herein, while providing a desired amount of shear fluid force via the inlet ports 320 and the outlet ports 325.

Figure 4:
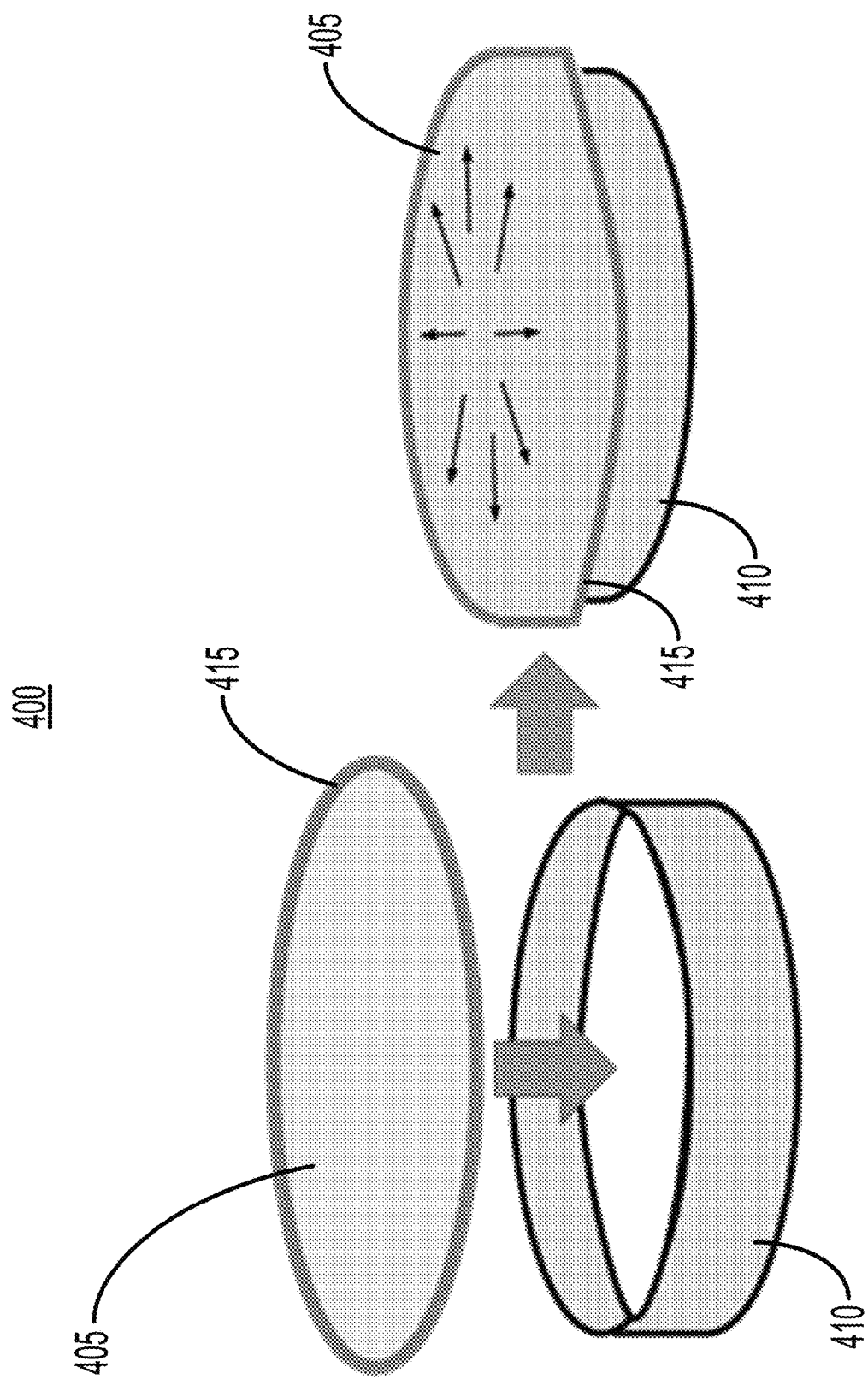
FIG. 4 illustrates an example design of a ring-type actuation technique for the highly deformable porous membrane culture systems described herein, in accordance with one or more implementations.

FIG. 4 illustrates a view 400 of an example design of a ring-type actuation technique for the highly deformable porous membrane culture systems described herein, in accordance with one or more implementations. As shown, deformable membrane 405 (which can be similar to and include all of the functionality of the deformable membranes 130, 250, and 350 described herein in connection with FIGS. 1, 2, and 3C, respectively) can be positioned and stretched over a rim 410. In a well plate environment, the rim 410 can be positioned beneath the deformable membrane 405 when the deformable membrane 405 is positioned within the well plate. In general, the depicted approach is based on the tensioning and tuning of a musical drum. Using the technique depicted in the view 400, the deformable membrane is affixed to a hoop 415, which can have a diameter that is greater than the rim 410. The hoop 415 and the rim 410 are moved relative to one another such that the deformable membrane is then stretched over the rim 410. The hoop 415 and rim 410 move relative to each other such that the membrane is pulled further down the rim 410 to achieve the desired amount of strain. The strain experienced by the deformable membrane 405 is mostly isotropic strain. Linear actuation of the hoop 415 and rim 410 motion can be accomplished by a variety of actuators, such as an electromechanical actuator, a magnetic actuator, a hydraulic actuator, or a pneumatic actuator, among others. The hoop 415 can form a part of an insert (e.g., the inserts 110, 210, and 310 described herein, etc.) to which the membrane is coupled. The rim 410 can form a part of an actuator positioned within a well plate beneath the hoop 415.

Figure 5:
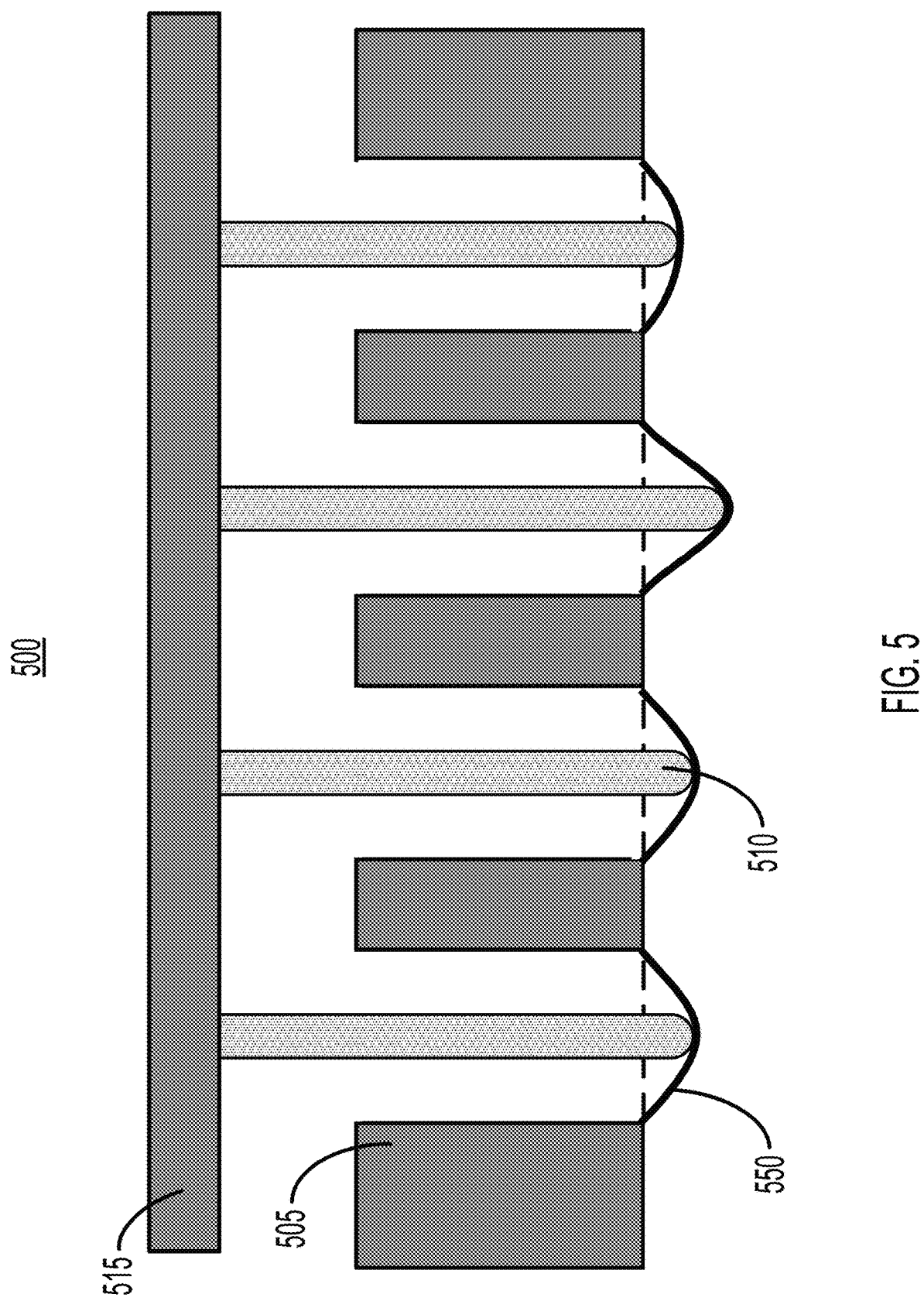
FIG. 5 illustrates a cross-sectional view of a pin-array type actuation technique for the highly deformable porous membrane culture systems described herein, in accordance with one or more implementations.

FIG. 5 illustrates a cross-sectional view 500 of a pin-array type actuation technique for the highly deformable porous membrane culture systems described herein, in accordance with one or more implementations. The pin-array type actuation technique can be used in connection with any of the well plates described herein, such as the well plate 105, 205, and 305, described herein in connection with FIGS. 1, 2, and 3A-3C. The view 500 depicts a well plate 505, a pin actuator device 515, one or more pins 510, and one or more deformable membranes 550. The well plate 505 can be similar to and include all of the functionality of the well plates 105, 205, and 305 described herein in connection with FIGS. 1, 2, and 3A-3C. Likewise, the deformable membrane 550 can include all of the functionality of the deformable membrane 130, 250, and 350 described herein in connection with FIGS. 1, 2, and 3C.

The pin actuator device 515 can include one or more actuators that can raise or lower the pins 510 by configurable amounts. The pin actuator device 515 can cause each of the pins to raise or lower independently from one another. The pin actuator can include one or more actuators for each pin 510, including an electro-mechanical actuator, a magnetic actuator, a hydraulic actuator, or a pneumatic actuator, among others. The pin actuator device 515 can press each pin 510 onto the center of each deformable membrane 550 to a precise depth. By pressing the pin into the deformable membrane 550 to the precise depth, the pin 510 can stretch the deformable membrane 550 by a desired amount of strain. The actuators in the pin actuator device 515 can allow individual control, such that each deformable membrane 550 can be stretched to a different desired strain. In some implementations, the pin actuator device 515 can form a part of the well plate 505. In some implementations, the pin actuator device 515, and the pins 510 coupled thereto, can be a separate device that is positioned precisely above the wells of the well plate 505. The pin actuation techniques described herein can be used in connection with any of the well plates described herein, including the well plate 105, 205, or 305. Although the deformable membranes 550 are show as forming part of a well in the well plate 505 in FIG. 5, it should be understood that the deformable membranes 550 can also be positioned in each well as part of an insert (e.g., the inserts 110, 210, or 310, etc.) as described herein.

Figure 6A:
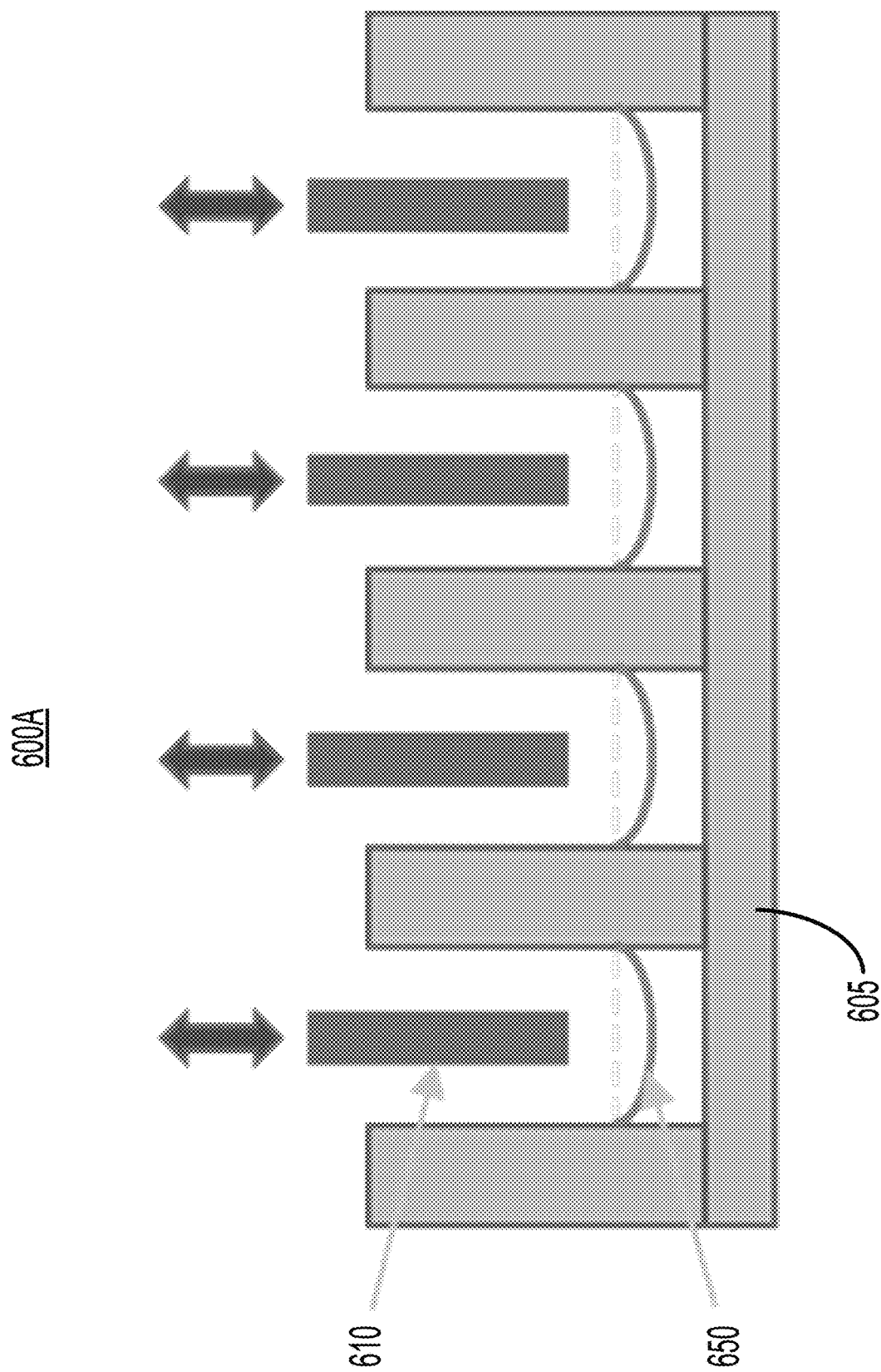
FIG. 6A illustrates a cross-sectional view of a magnet array type actuation technique for the highly deformable porous membrane culture systems described herein, in accordance with one or more implementations.

FIG. 6A illustrates a cross-sectional view 600A of a magnet array type actuation technique for the highly deformable porous membrane culture systems described herein, in accordance with one or more implementations. The view 600A shows a well plate 605 (which can be similar to and include all of the functionality of the well plates 105, 205, 305, and 505 described herein in connection with FIGS. 1, 2, 3A-3C, and 5), one or more deformable membranes 650 (which can include all of the functionality of the deformable membranes 130, 250, and 350, described herein in connection with FIGS. 1, 2, and 3C), and one or more magnetic pins 610. The magnetic pins 610 can be coupled to a pin actuator (not pictured) that can independently raise and lower each of the magnetic pins to precise distances from the deformable membranes 650.

In addition to the functionality described herein, in a magnetic actuation system, each of the deformable membranes 650 can include one or more ferromagnetic elements embedded therein. Magnetic actuation can allow for a non-contact method of deforming the deformable membrane 650 with reduced mechanical complexity. The deformable membrane 650 can be embedded with one or more magnetic or ferromagnetic particles or beads encapsulated in an inert material. Thus, the particles would not necessarily contact or affect the cell cultures disposed on the deformable membrane 650. The magnetic particles can be dispersed through the membrane in a controlled configuration, which can be optimized to cause desired uniform strain across the deformable membrane 650. An array of magnetic or electromagnetic pins 610 can then be brought into appropriate proximity to the deformable membrane 650, resulting in attraction or repulsion. The magnetic pin can generate a magnetic field that exerts a force on the particles in the deformable membrane 650, causing the deformable membrane to stretch by the desired amount of strain. The membrane strain and displacement can optimized by precise placement of the particles.

In some implementations, a ferrous mechanical feature (not pictured) can be included on top of, affixed to the bottom, or embedded within the deformable membrane 650. This mechanical feature could be a ring, toroid or other circular shape. In some implementations, the ferrous mechanical feature can be a set of features, such as a circle of small objects affixed around the perimeter of the deformable membrane 650. A detent or mechanical holding apparatus (not pictured0 can be positioned within the well plate 605. The detent or mechanical holding apparatus can limit the amount by which the deformable membrane 650 can stretch. The detent can be a ledge, a barrier, or a surface feature that limits the amount of distance the membrane can stretch. The detent can also be configured in steps, ramps, or other ways to progressively or incrementally increase or decrease the resistance of the membrane to motion, strain, or stretch. In some implementations, the magnetic pins 610 can be an electromagnet with an adjustable magnetic field. The magnetic field of each magnetic pin 610 can be adjusted by changing the current, voltage, duty cycle, frequency, or other parameter of the electrical signal that creates the electromagnet.

Figure 6B:
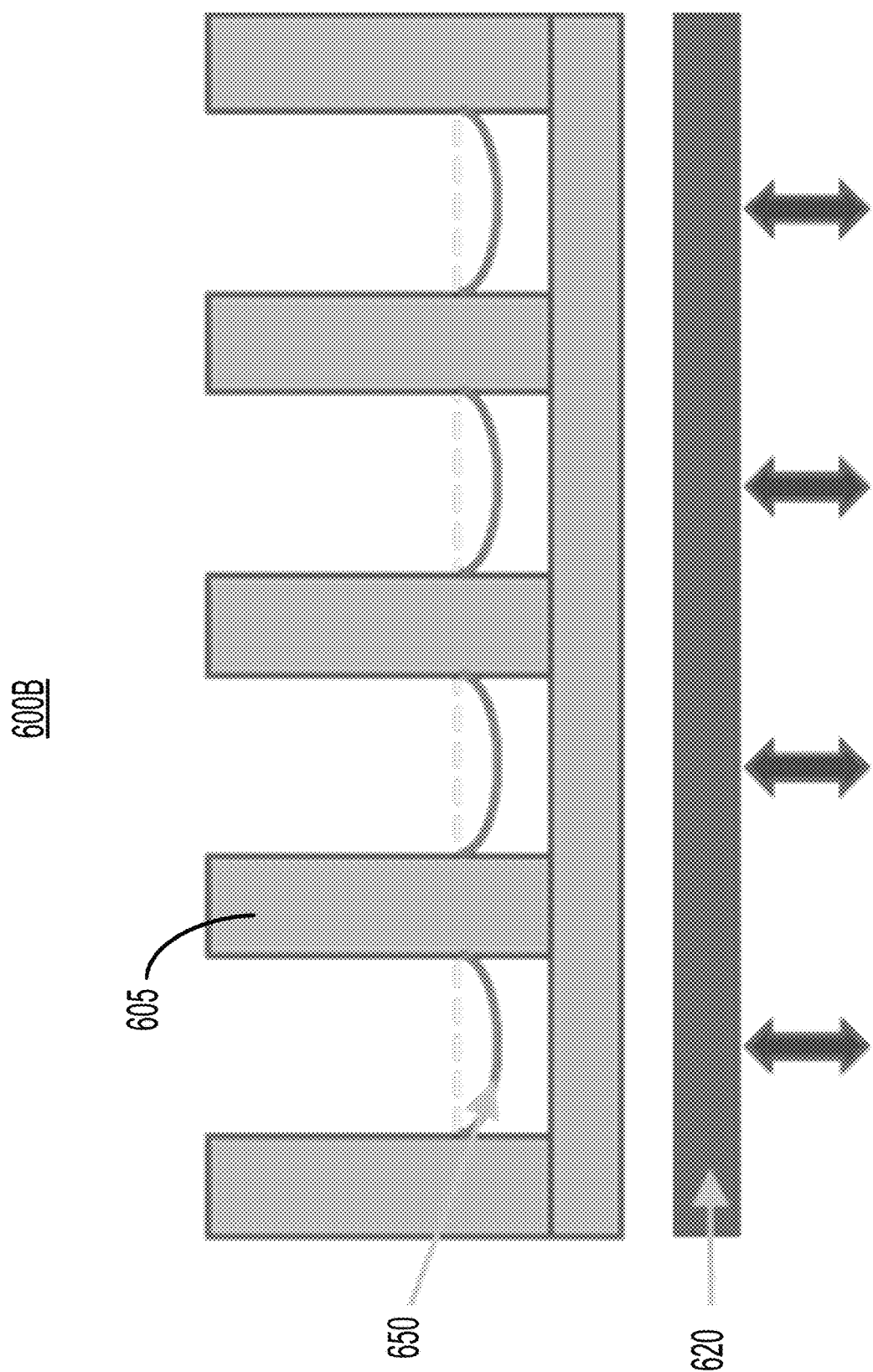
FIG. 6B illustrates a cross-sectional view of a single magnet type actuation technique for the highly deformable porous membrane culture systems described herein, in accordance with one or more implementations.

FIG. 6B illustrates a cross-sectional view 600B of a single magnet type actuation technique for the highly deformable porous membrane culture systems described herein, in accordance with one or more implementations. The view 600B shows a similar arrangement to the components depicted in the view 600A of FIG. 6A, but instead of individual magnetic pins 610, a single magnet 620 is used. The magnet 620 can be similar to the magnetic pins 610 described herein above in connection with FIG. 6A. The magnet 620 can be brought a precise distance from each of the deformable membranes 650 of the well plate 605, to cause the deformable membranes 650 to stretch based on the magnetic field created by the magnet 620. Much like the magnetic pins 610, the magnet 620 can be an electromagnet with a configurable magnetic field strength. In addition, the magnet 620 can be actuated to bring the magnet to a desired distance from the deformable membranes 650 positioned in the well plate 605. Although the deformable membranes 650 are show as forming part of a well in the well plate 605 in FIGS. 6A and 6B, it should be understood that the deformable membranes 650 can also be positioned in each well as part of an insert (e.g., the inserts 110, 210, or 310, etc.) as described herein.

Figure 7B:
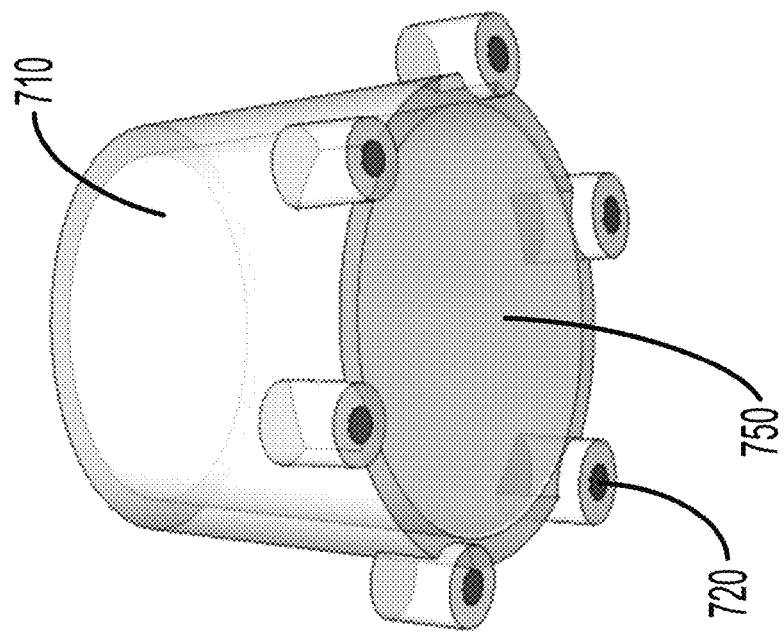
FIGS. 7A and 7B illustrate perspective views of an example actuation technique using a flexible insert with magnetic coupled thereto, in accordance with one or more implementations.
Figure 7A:
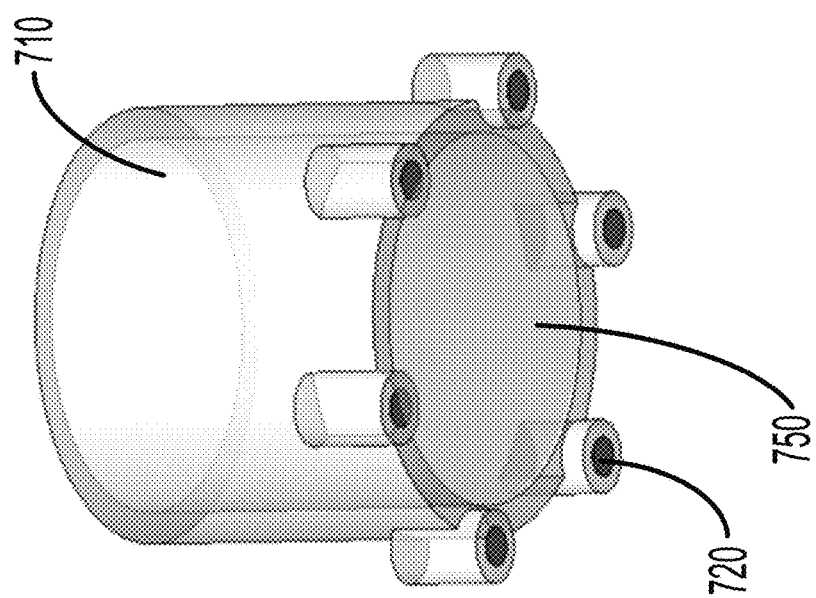

FIGS. 7A and 7B illustrate perspective views 700A and 700B of an example actuation technique using a flexible insert 710 with magnetic coupled thereto, in accordance with one or more implementations. The view 700A shows an insert 710 (which can include all of the structure and functionality of one or more of the inserts 110, 210, or 310, described herein in connection with FIGS. 1, 2, and 3A-3C, etc.) that is coupled to a deformable membrane 750 (which can include all of the functionality of the deformable membranes 130, 250, and 350, described herein in connection with FIGS. 1, 2, and 3C) and coupled to one or more magnetic portions 720. The magnetic portions 720 can be inserted into or coupled to one or more standoff feet positioned at the end of the insert 710 to which the deformable membrane 750 is coupled.

In this implementation of a magnetic actuation system, the deformable membrane 750 can be deformed by way of the insert 710 changing change due to an external force. Here, that external force can be provided by the magnetic portions 720 coupled to the base of the insert 710. The magnetic portions 720 can be, for example, one or more magnets that are embedded in the insert 710 forming standoff "feet" that rest on the bottom of a well of a well plate when the insert 710 is positioned in the well plate. As shown, the deformable membrane 750 is attached to the bottom portion of the insert 750, and is also positioned near the bottom of the well of the well plate when the insert 710 is positioned in the well. Each of the magnetic portions 720 can be coupled to one or more external magnets that are positioned in or on the other side of the well. Each of the external magnets (described in further detail herein below in connection with FIGS. 7C and 7D) can be mounted to an actuator that moves the magnets out radially. The actuator can be any sort of actuator, and can include electromechanical elements such as an iris actuator or any other sort of actuator. The insert 710 can be manufactured from a flexible material, such as a stretchable plastic that is rigid enough to return to its original shape when external stretching forces are removed.

As shown in the view 700B, the insert 710 can be a flexible insert that can deform in response to an external force, and return to its original shape when the external force is removed. Because the edges of the deformable membrane 750 are coupled to the bottom edges of the insert 710, radial expansion (e.g., as shown in the view 700B, etc.) of the bottom portion of the insert 710 causes the membrane 750 to stretch. By varying the degree to which the insert 710 is deformed (e.g., by moving the external magnets as described herein, etc.), a desired amount of strain or stretch can be achieved at the deformable membrane 750 surface. Thus, by deforming the insert 710 by applying an external magnetic field to one or more of the magnetic portions 720, the deformable membrane can be deformed to a desired amount of strain or stretch. In some implementations, the magnetic portions 720 can be ferromagnetic materials that are not necessarily magnetic themselves (e.g., pieces of iron, or other magnetic materials, etc.). Implementations of the magnetic actuation techniques shown in the views 700A and 700B are shown in use in a well plate in FIGS. 7C and 7D.

Figure 7D:
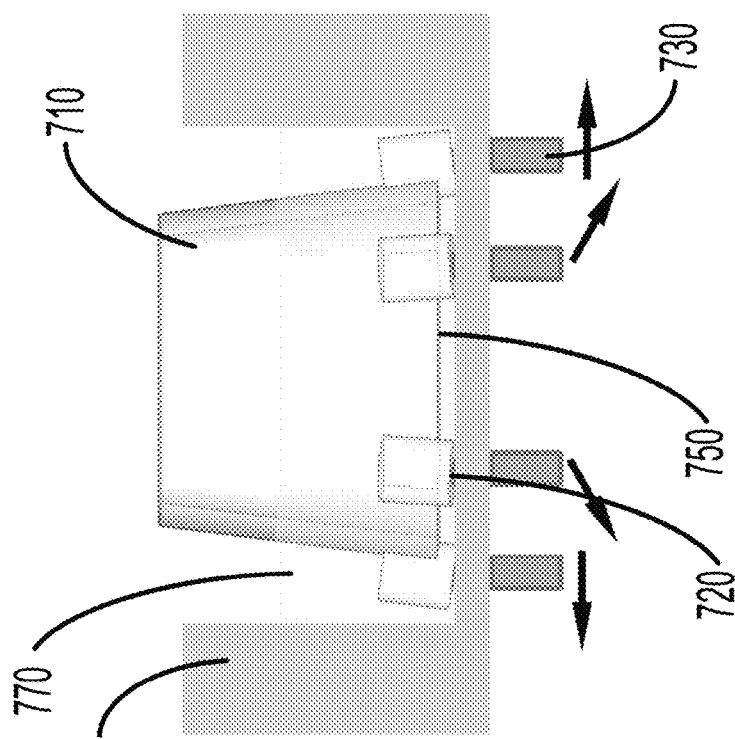
FIGS. 7C and 7D illustrate cross-sectional views of the example actuation technique shown in FIGS. 7A and 7B, in accordance with one or more implementations.
Figure 7C:
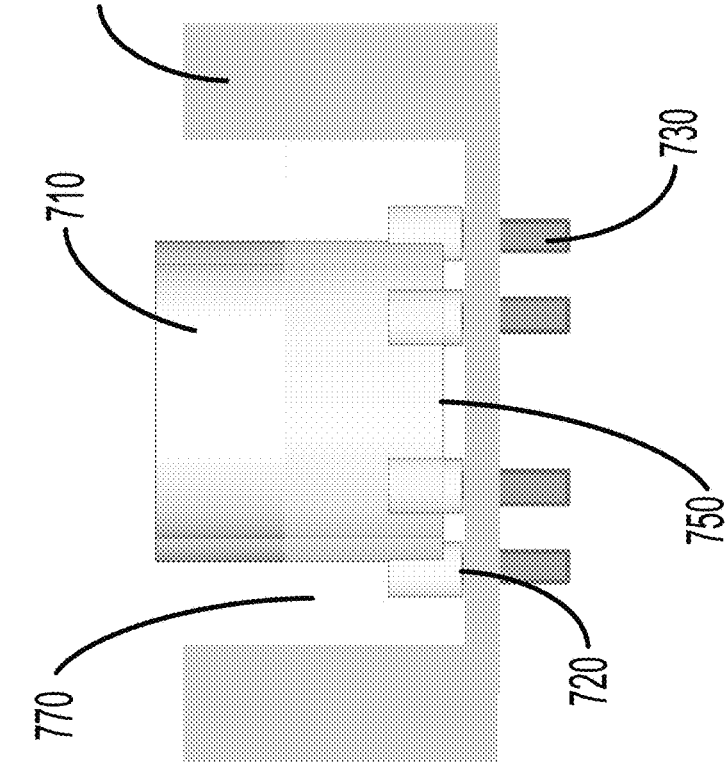

FIGS. 7C and 7D illustrate cross-sectional views 700C and 700D of the example magnetic actuation technique shown in FIGS. 7A and 7B, in accordance with one or more implementations. As shown, the insert 710 can be inserted into a well plate 705 (which can be similar to and include any of the structure and functionality of one or more of the well plates 105, 205, 305, 505, or 605 as described herein), and can be partially submerged in a culture media 770 (which can be similar to and include any of the structure and functionality of the culture media 115 or 355 described herein). As shown, the portions of the insert 710 to which the magnetic portions 720 are coupled can form one or more standoffs, which cause the magnetic portions 720 to contact the bottom of the well while the deformable membrane 750 is suspended above the bottom of the well in the culture media 770. The external magnets 730 can be positioned outside of the well on a surface opposite that of the magnetic portions 720 coupled to the insert 710. Each of the external magnets 730 can be coupled to one or more actuators.

As shown in the view 700D, the external magnets 730 can be repositioned by the one or more actuators. Because the external magnets 730 are magnetically coupled to the magnetic portions, movement of the external magnets 730 can cause corresponding movement of the magnetic portions 720 of the insert 710. Thus, when the external magnets 730 are moved outward radially, the magnetic portions 720 coupled to the insert 710 can deform the flexible insert 710 outward at the bottom of the flexible insert 710. Because the edges of the deformable membrane 750 are coupled to the edges of the bottom portion of the insert 710, the deformation in the flexible insert 710 causes corresponding deformation in the deformable membrane 750. Thus, by controlling the positions of the external magnets 730, the deformable membrane 750 can be deformed by the desired amount of stretch or strain.

Figure 8B:
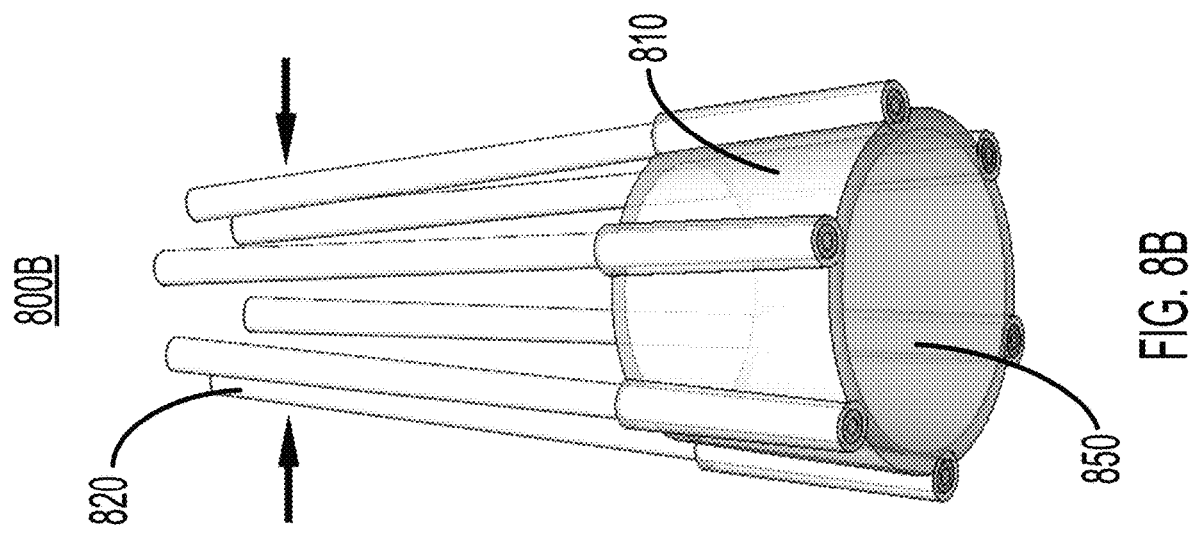
FIGS. 8A and 8B illustrate perspective views of an example actuation technique using a flexible insert with one or more pins coupled thereto, in accordance with one or more implementations.
Figure 8A:
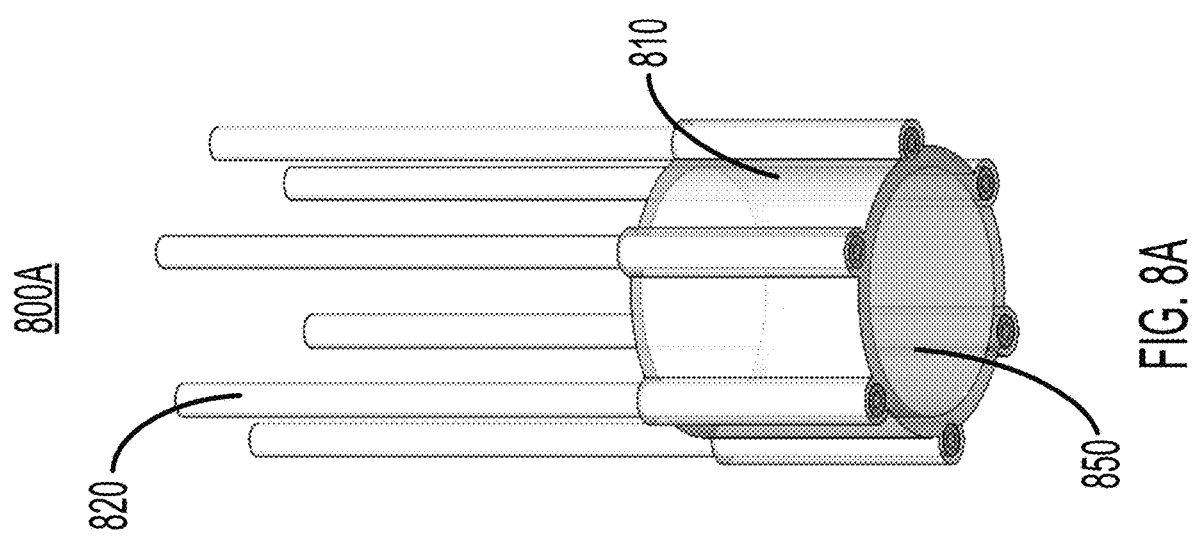

FIGS. 8A and 8B illustrate perspective views 800A and 800B, respectively, of an example actuation technique using a flexible insert with one or more pins coupled thereto, in accordance with one or more implementations. The view 800A shows an insert 810 (which can include all of the structure and functionality of one or more of the inserts 110, 210, 310, or 710 described herein in connection with FIGS. 1, 2, 3A-3C, and 7, etc.) that is coupled to deformable membrane 850 (which can include all of the functionality of the deformable membranes 130, 250, 350, and 750, described herein in connection with FIGS. 1, 2, 3C, and 7) and coupled to one or more pins 820 around the exterior of the insert. The pins can extend perpendicular to the base of the insert 810, and can be coupled to the insert 720 along a vertical axis of the insert 810.

In this implementation of a pin-based actuation system, the deformable membrane 850 can be deformed by way of the insert 810 changing shape due to an external force. Here, that external force can be provided by the pins 820 coupled to the exterior of the insert 810. The pins 820 can be, for example, one or more rigid, vertically arranged rods that are coupled to or inserted into the outer walls of the insert 810. In some implementations, the bottom of the pins 820 can be flush with the bottom of the insert 810. When positioned in a well of a well plate (e.g., such as any of the well plates described herein, etc.), the insert can be suspended such that the bottom of the insert 810 (and therefore the deformable membrane 850, etc.) does not contact the bottom portion of the well plate. As shown, the deformable membrane 850 is attached to the bottom portion of the insert 850, and is therefore also positioned near the bottom of the well of the well plate when the insert 810 is suspended in the well. Each of the pins 820 can be coupled to one or more pins 820 can be coupled to an actuator that can move the pins 820 inward the magnets out radially. The actuator can be any sort of actuator, and can include electromechanical elements such as an iris actuator or any other sort of actuator. The insert 810 can be manufactured from a flexible material, such as a stretchable plastic that is rigid enough to return to its original shape when external stretching forces are removed.

As shown in the view 800B, the insert 810 can be a flexible insert that can deform in response to an external force, and return to its original shape when the external force is removed. Because the edges of the deformable membrane 850 are coupled to the bottom edges of the insert 810, radial expansion (e.g., as shown in the view 800B, etc.) of the bottom portion of the insert 810 causes the membrane 850 to stretch. By varying the degree to which the insert 710 is deformed (e.g., by moving the external magnets as described herein, etc.), a desired amount of strain or stretch can be achieved at the deformable membrane 750 surface. Thus, by deforming the insert 810 by applying an external force to one or more of the pins 820, the deformable membrane 850 can be deformed to a desired amount of strain or stretch. In some implementations, and as shown in the view 800B, the top of the pins 820 can be forced inward, causing the pins 820 to pivot such that the bottom of the pins 820 are forced outward. This outward force is applied to the bottom of the insert 810, causing the deformable membrane 850 to stretch. Implementations of the pin-based actuation techniques shown in the views 800A and 800B are shown in use in a well plate in FIGS. 8C and 8D.

FIGS. 8C and 8D illustrate cross-sectional views of the example actuation technique shown in FIGS. 8A and 8B, in accordance with one or more implementations. As shown, the insert 810 can be inserted into a well plate 805 (which can be similar to and include any of the structure and functionality of one or more of the well plates 105, 205, 305, 505, 605, or 705 as described herein), and can be partially submerged in a culture media 870 (which can be similar to and include any of the structure and functionality of the culture media 115, 355, or 770 described herein). As shown, the pins 820 are coupled to the exterior of the insert 810, and can be flush against the bottom of the insert 810. In some implementations, the pins 820 are not flush with the bottom of the insert 810, and instead can project downward forming one or more standoffs. As shown, the insert 810 can be suspended in the well such that the bottom of the insert 810, and therefore the deformable membrane 850, is suspended above the bottom of the well in the culture media 870. In some implementations, the insert 810 can be suspended in the well plate 805 by the one or more pins 820. For example, the pins 820 can each be coupled to one or more actuators (not pictured), which can be positioned above the well plate 805. Because the pins 820 are securely coupled to the insert 810, the pins 820 can suspend the insert 810 above the bottom of the well plate 805.

As shown in the view 800D, the top of the pins 820 (e.g., a portion coupled to an actuator, etc.) can be repositioned by the one or more actuators. Because the pins 820 are coupled to the outer edge of the insert 810, movement of the pins 820 can cause corresponding movement of the insert 810. Thus, when the top of the pins 820 are moved inward radially (e.g., as pictured, etc.), the bottom of the insert 810 can deform and stretch outward radially. Because the edges of the deformable membrane 850 are coupled to the edges of the bottom portion of the insert 810, the deformation in the flexible insert 810 causes corresponding deformation in the deformable membrane 850. Thus, by controlling the positions of the pins 820 (e.g., using one or more actuators, etc.), the deformable membrane 850 can be deformed by the desired amount of stretch or strain.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations.

The phraseology and terminology used herein is for the purpose of description and should not be regarded as limiting. The use of "including", "comprising", "having", "containing", "involving", "characterized by", "characterized in that", and variations thereof herein is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which they are used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description, or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A well plate for actuating cell culture membranes, comprising:
   a well comprising a first opening;
   an insert comprising a wall and a deformable membrane positioned in the first opening of the well, the insert comprising an opening exposing a first surface of the deformable membrane, the wall of the insert comprising a flexible material coupled to the deformable membrane;
   a chamber defined beneath the well, the chamber configured to receive fluid media and to expose the fluid media to a second surface of the deformable membrane positioned in the well, the second surface opposite the first surface; and
   an actuator at least partially coupled to the wall of the insert, the actuator configured to deform the flexible material of the wall of the insert to stretch the deformable membrane by an amount of strain.

2. The well plate of claim 1, further comprising a gasket positioned within the well and configured to create a seal between the insert and the well.

3. The well plate of claim 2, wherein the gasket further comprises an O-ring and a collar, the collar configured to couple the insert to the well and the O-ring configured to create a seal between the collar and the well.

4. The well plate of claim 1, wherein a surface of the chamber is defined by a transparent window that provides an optical interface to the chamber and to the second surface of the deformable membrane positioned in the well.

5. The well plate of claim 1, wherein the well further comprises a connector configured to receive and couple to the insert.

6. The well plate of claim 1, wherein the actuator comprises a mechanical iris configured to couple to the insert, and to radially stretch the deformable membrane by the amount of strain.

7. The well plate of claim 1, further comprising:
   a second well comprising a second opening;
   a second insert coupled to a second deformable membrane positioned in the second opening; and
   a second actuator comprising a rim that is similar in size to a boundary of the second deformable membrane of the second insert, and is configured to cause the second deformable membrane to stretch over the rim by a second amount of strain.

8. The well plate of claim 1, further comprising:
   a second well comprising a second opening;
   a second insert coupled to a second deformable membrane positioned in the second opening; and
   a second actuator comprising a pin configured to press into the second deformable membrane of the second insert, such that the pin deforms the second deformable membrane by a second amount of strain.

9. The well plate of claim 1, further comprising:
   a second well comprising a second opening;
   a second insert coupled to a second deformable membrane positioned in the second opening; and
   a second actuator comprising a magnet positioned within a predetermined distance from the second insert, such that a magnetic force between the magnet and one or more magnetic particles in the second deformable membrane causes the second deformable membrane to stretch by a second amount of strain.

10. The well plate of claim 1, wherein the chamber further comprises an inlet port configured to couple to a pressure controller that provides the fluid media at a pressure, the inlet port configured to receive the fluid media such that the fluid media causes the deformable membrane of the insert to stretch by the amount of strain.

11. The well plate of claim 1, further comprising:
   a second well comprising a second opening;
   a second insert coupled to a second deformable membrane; and
   a second actuator configured to stretch the second deformable membrane by a second amount of strain.

* * * * *